United States Patent [19]

Silver

[11] 4,210,722
[45] Jul. 1, 1980

[54] PROTEIN IMMOBILIZER

[75] Inventor: Spencer F. Silver, White Bear Lake, Minn.

[73] Assignee: Minnesota Mining and Manufacturing Company, St. Paul, Minn.

[21] Appl. No.: 851,492

[22] Filed: Nov. 14, 1977

[51] Int. Cl.$^2$ .................. C07G 7/02; C07G 7/00
[52] U.S. Cl. .................. 435/176; 23/230 B; 252/428; 260/112 R; 310/311; 424/12; 435/7; 435/180
[58] Field of Search .......... 195/63, 68, DIG. 11; 260/112 R, 32.6 A; 252/428, 430; 435/176, 177, 180, 7; 23/230 B; 424/12; 310/311

[56] References Cited

U.S. PATENT DOCUMENTS

| | | | |
|---|---|---|---|
| 3,705,084 | 12/1972 | Reynolds | 195/63 |
| 3,740,414 | 6/1973 | Olson | 260/32.6 A |
| 3,796,634 | 3/1974 | Haynes et al. | 195/63 |
| 3,844,892 | 10/1974 | Matthews | 195/63 X |
| 4,048,018 | 9/1977 | Coughlin et al. | 195/63 X |
| 4,071,409 | 1/1978 | Messing et al. | 195/63 |
| 4,072,566 | 2/1978 | Lynn | 195/63 |

*Primary Examiner*—David M. Naff
*Attorney, Agent, or Firm*—Cruzan Alexander; Donald M. Sell; Carolyn A. Bates

[57] ABSTRACT

Biologically active proteins are immobilized on polar supports by first applying to the support a monolayer of a water-soluble polymer containing a β-hydroxyalkyleneamine moiety wherein the equivalent weight of the polymer based on the β-hydroxyalkyleneamine moiety is 87 to about 10,000. The protein irreversibly attaches to the polymer-treated support and retains substantially all of its biological activity.

30 Claims, No Drawings

PROTEIN IMMOBILIZER

This invention relates to the field of immobilized proteins, particularly to enzymes and immunologically-active proteins (immunochemicals) which have been irreversibly attached to solid supports.

The desirability of immobilizing enzymes on insoluble supports has long been recognized. Unless immobilized, watersoluble enzymes cannot be economically recovered from reaction mixtures in which they are used. By immobilizing the enzyme on a solid support or carrier, the enzyme can be readily separated from the reaction mixture and reused. Furthermore, immobilized enzymes are generally less susceptible to denaturation, i.e., loss of activity, by chemical attack, pH and temperature changes, etc. than are free enzymes.

Likewise, it is often desirable to immobilize immunologically-active proteins, e.g., antigens and antibodies, to improve immunological test procedures. Most immunological tests are based upon complex formation between an antigen and its corresponding antibody. In many cases the presence of the complex in a fluid sample is indiscernible unless one of the reacting immunochemicals is bound to a particulate support such as polystyrene latex. In other tests it is desirable to physically separate the complex from the fluid sample. This procedure is simplified by attaching one of the reacting immunochemicals to a solid support.

Heretofore, a number of methods have been used to immobilize proteins, each with its attendant disadvantages. One common method of immobilizing proteins is by direct physical adsorption onto an inert support such as glass beads, charcoal, or other high energy surfaces. Generally, the protein is attached to these supports by strong bonds which tend to denature and deactivate the proteins.

Another method of immobilizing proteins, especially enzymes, is by physical entrapment in a polymeric matrix such as a crosslinked polyacrylamide gel. The principal disadvantages of this method include inaccessibility of large molecules to the enzyme and leaking of the enzyme out of the polymer matrix.

To enhance the stability of the suport-protein composite, methods for both ionically and covalently bonding the protein to the support have been developed. U.S. Pat. No. 3,915,797 discloses an enzyme-support composite in which the support is a water-insoluble crosslinked anion-exchange resin consisting of a block copolymer of styrene and a quaternized vinylpyridine. Such polymers have limited utility as they are restricted in configuration to gel particles. The bond between the enzyme and the resin is said to be a combination of ionic adsorption and covalent bonding. Other gel particles useful for immobilizing enzymes consist of polymers having chelating sites defined by pairs of adjacent hydroxy and carboxylic acid groups are disclosed in U.S. Pat. No. 3,794,563.

U.S. Pat. No. 3,705,084 discloses a macroporous enzyme reactor wherein the enzyme is attached to a macroporous core with a polymeric surface having adsorption promoting groups of the class consisting of nitrilo, acid amido and ureido. Enzymes adsorbed on these polymeric surfaces require further immobilization by crosslinking in place with a difunctional reagent such as glutaraldehyde or other dialdehydes.

Another material used to couple proteins to solid supports is a solution of o-dianisidine as described in U.S. Pat. No. 3,983,000. This material is limited to use with inorganic supports having available oxide or hydroxyl surface groups. Although the protein may be directly bonded to the o-dianisidine-treated support, it is also suggested that the o-dianisidine residue may be modified with a chemical such as glutaraldehyde prior to reaction with the protein in order to overcome the inherent oxidative instability of aromatic amines.

U.S. Pat. No. 3,494,775 discloses water-soluble amines having a molecular weight less than 5,000 and containing at least two amine-reactive epichlorhydrin residues per molecule as latent insolubilizing agents for film-forming proteins in fluid aqueous paper and film-forming compositions. The insolubilizing agent and the protein are mixed together and cured. The protein and epoxy residues interact to form a crosslinked gel in much the same fashion as glutaraldehyde is used to crosslink proteins in place.

In general, prior art methods of attaching proteins to solid supports have required chemical reactions between the prctein and surface of the support in order to achieve strong binding and enhance the stability of the composite. Such chemical reactions are undesirable in that they may reduce the biological activity of the protein and they may not achieve uniform coverage of the support with the protein.

The present invention overcomes many of the disadvantages of prior art methods of immobilizing proteins by providing a polymer which can be easily applied to a variety of supports and which irreversibly binds proteins thereto without the need for further chemical modification or surface reactions and without affecting the biological activity of the proteins. Furthermore, an enzyme-support composite which is stable to storage is provided.

According to the present invention there is provided a method of immobilizing biologically active proteins on a solid polar support while retaining substantially all of their biological properties comprising the steps of: (1) applying to the support a monolayer of a water-soluble polymer containing a $\beta$-hydroxyalkyleneamine moiety wherein the equivalent weight of the polymer based on said moiety is 87 to about 10,000; and (2) contacting the treated support with an aqueous solution of a protein. An article comprising a polar support having a monolayer of the $\beta$-hydroxyalkyleneamine containing polymer on the surface thereof is also included within the scope of the invention, as is the composite article comprising the polymer-treated polar support and a biologically active protein attached thereto.

The present invention provides a simple and effective method of irreversibly attaching proteins to solid supports while maintaining substantially all the biological activity of the protein. The method is versatile in that a variety of polar supports may be used. Such support materials can be of a variety of configurations such as, screens, cloth, beads, tubes, fritted discs, etc. Also, they can have a variety of handling characteristics, i.e., had, rigid, woven or non-woven flexible webs or the like. Uniform coverage of the support is achieved, and no chemical modification of the protein is required. Furthermore, the protein-support composite retains its useful properties for long periods of time and does not show oxidative instability or decay of chemically-reactive pendant groups which are characteristic of most prior art materials. Proteins of all types, including enzymes and immunologically active proteins may be immobilized on solid supports according to the present invention.

The term "polar support" as used in the context of the present invention refers to those surfaces wettable by water including metals, metal oxides, glasses, ceramics, clays and insoluble hydrophilic proteinaceous materials. The term "monolayer" means a thin layer approximately 10 to 250 angstroms thick, with the preferred thickness being in the range of 10 to 100 angstroms.

The β-hydroxyalkyleneamine-containing polymers useful in the practice of the invention are water-soluble and contain the moiety

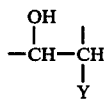

Formula I wherein Y is an amine group. The equivalent weight of the polymer based on this moiety is 87 to about 10,000. The amine group may be pendant from the polymer backbone, in which case preferred moieties may be represented by the formula

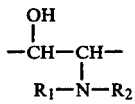

Formula II wherein $R_1$ is hydrogen or alkyl having one to eight carbon atoms, $R_2$ is alkyl having one to eight carbon atoms or $R_1$ and $R_2$ taken together with the nitrogen atom to which they are attached form a heterocyclic ring. Alternatively, the amine group may be part of the polymer backbone as in the following preferred moieties

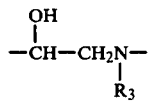

Formula III wherein $R_3$ is hydrogen or alkyl, having one to eight carbon atoms.

An especially preferred class of β-hydroxyalkyleneamine-containing polymers for use according to the present invention are synthesized by epoxidizing butadiene polymer followed by amination as described in U.S. Pat. No. 3,740,414, yielding polymers having the repeating unit

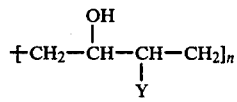

wherein Y is as defined above in Formula I. Random and block copolymers of butadiene and other copolymerizable monomers such as styrene may also be aminated to form protein-immobilizing agents according to the invention. The amine groups forming the Y-portion of the polymer are preferably derived from piperidine, morpholine, dimethylamine, diethylamine and diethanolamine.

Another class of preferred polymers for use according to the invention is prepared by polymerizing epichlorohydrin and methyl amine according to U.S. Pat. No. 3,732,173 and contain the repeating unit

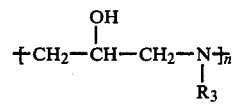

wherein $R_3$ is as defined above in Formula III.

Aminated glycidyl polyacrylates and glycidyl polymethacrylates are also useful and contain the repeating unit

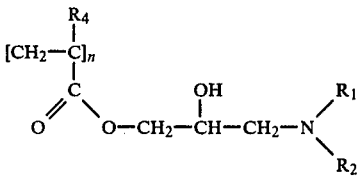

Formula IV wherein $R_4$ is hydrogen or methyl and $R_1$ and $R_2$ are as defined above in Formula II.

Especially preferred polymers for practicing the invention are formed from: (1) the dimethylamine adduct of epoxidized poly-cis-1,4-butadiene; (2) the dimethylamine adduct of epoxidized styrene-b-butadiene; (3) the dimethylamine adduct of polyglycidyl methacrylate; (4) the piperidine adduct of epoxidized styrene-b-butadiene; (5) the piperidine adduct of poly-cis-1,4-butadiene; and (6) the condensation product of epichlorohydrin and methylamine.

The β-hydroxyalkyleneamine-containing polymers have molecular weights ranging from 1000 to several million. However, the preferred molecular weight is in the range of 10,000 to 250,000. As molecular weight is increased above about 250,000, the aminated polymers create preparative problems.

The optimum level of β-hydroxyalkyleneamine moieties in the polymer is somewhat related to molecular weight. A sufficient amount of the moiety must be present in order to render the polymer water-soluble. Low molecular weight polymers will require fewer β-hydroxyalkyleneamine moieties to inesure watersolubility. Preferably, at least 30 percent of the polymer repeating units will contain the moiety.

The polymer is deposited onto the polar support from a dilute aqueous solution. Generally, solutions containing 0.03 to 0.5 percent polymer (w/w) are used.

Suitable polar supports for use according to the invention include siliceous materials such as sand, glass or quartz; metals such as aluminum, steel and silver; ceramics; inorganic powders such as oxides and barrium ferrite; proteins; polymers containing acid residues, and the like. The support may have any shape and may include particulate or fibrous substances.

The β-hydroxyalkyleneamine polymer is deposited as a monolayer on the surface of the substrate by immersing the substrate in a dilute aqueous solution of the polymer for 30 seconds to 24 hours followed by a water wash. The support may be dried and stored or used immediately to contact an aqueous solution of the protein to be immobilized. Deposition of the protein on the polymer-support composite is preferably accomplished by immersion of the support in the protein solution. The optimum concentration of the protein solution will vary depending on the protein immobilized. Generally, protein solutions in the range of 0.5 to 100 mg/ml will be used. Following an equilibration period of a few seconds to 24 hours, the support is removed from the protein solution and washed with water.

The polymer-primed support is capable off immobilizing in an essentially irreversible manner a wide variety of proteins. Although the exact mechanism by which the protein attaches to the polymer surface of the support is not known, it is believed that such attachment results from coordinate covalent bonds between the amine-hydroxy functionality of the polymer and the protein.

Enzymes immobilized on β-hydroxyalkyleneamine-coated particulate or fibrous supports as described herein, are useful in enzymatic chemical processing in the conventional manner. Examples thereof include the use of glucose isomerase in the conversion of glucose to fructose, and the use of lactase in the removal of lactose during the isolation of proteins from cheese whey. Further examples of enzymes which can be strongly attached to the β-hydroxyalkyleneamine polymers include urease, glucose oxidase, invertase, catalase, papain, lipase, cellulase, dextranase, amylase, ribonuclease, carboxypeptidase and urokinase.

Immunochemicals such as antigens and antibodies may be conveniently attached to supports according to the invention and used in conventional manner for immunological testing. Examples of supports to which these materials may be attached include glass, quartz, ceramics, metal oxides and proteins. An especially preferred support is a piezoelectric oscillator, e.g. quartz crystal oscillator as described in copending application Ser. No. 851,491, filed Nov. 14, 1977 and assigned to the same assignee as the present application.

Examples of immunologically-active proteins which may be immobilized according to the invention include gamma globulins, haptoglobin, $\alpha_1$-antitrypsin inhibitor, serum albumin transferrin, compliment and $\alpha$-globulins.

The invention may be further illustrated by the following nonlimiting examples.

Examples 1-6 illustrate the preparation of polymers of Formula II.

EXAMPLE 1

Into a 250 ml round bottom flask equipped with a stirrer and reflux condenser were placed 100 g of a 7.36 percent solids solution in dioxane of epoxidized styrene (45M)/butadiene(105M) block copolymer (epoxy equivalent 106). Piperidine (25 g), was added and the solution was kept under reflux with stirring overnight. Most (~80%) of the dioxane was removed by distillation in vacuo and 500 ml of methanol were added. This solution was concentrated in vacuo to semidryness and the residue dissolved in methanol to yield a 1% solid solution.

% $N_2$: Calc. —6.32%; Found —4.2%

EXAMPLES 2-6

Following the general procedure outlined in Example 1, the following β-hydroxyalkyleneamine derivatized polymers of Formula I were prepared:

| Example | Epoxide Derivative of: | Amine Reactant | % N in Adduct |
|---|---|---|---|
| 2 | Styrene (MW45,000)/cis-1,4-butadiene (MW105,000) | morpholine | 5.2 |
| 2A | Styrene (MW45,000)/cis-1,4-butadiene (MW105,00) | diethylamine | 1.5 |
| 3 | Styrene (MW75,000)/cis-1,4-butadiene (MW75,000) | piperidine | 3.6 |
| 4 | Styrene (MW90,000)/cis-1,4-butadiene (MW60,000) | n-propylamine | 2.2 |
| 4A | Styrene (MW90,000)/cis-1,4-butadiene (MW60,000) | piperidine | 4.3 |
| 5 | (Poly(cis-1,4-butadiene) (MW92,000) | n-propylamine | 4.3 |
| 5A | Poly(cis-1,4-butadiene) (MW92,000) | piperidine | 6.4 |
| 5B | Poly(cis-1,4-butadiene) (MW92,000) | dimethylamine | 2.5 |
| 6 | Poly(cis-1,4-butadiene) (MW200,000) | n-propylamine | 5.2 |
| 6A | Poly(cis-1,4)butadiene) (MW200,000) | piperidine | 4.5 |

Examples 7-9 illustrate the preparation of polymers of Formula IV in which the β-hydroxyalkyleneamine group is pendant to the polymer backbone.

EXAMPLE 7

To a dioxane solution of poly(glycidyl methacrylate) containing 5 g of polymer were added 5.0 ml (large excess) of redistilled piperidine. The mixture was kept under reflux with stirring overnight, then diluted with 500 ml of methanol. The volume was reduced to ~100 ml in vacuo. This was repeated with 500 ml methanol, and sufficient methanol was added to the residue to yield a 5 percent solid solution.

% $N_2$: Calc. —6.16%; Found—6.2%

Following the general procedure outlined in Example 7, the following polymers were synthesized:

| Ex. | Epoxide Derivative of: | Amine Reactant | % N in Adduct |
|---|---|---|---|
| 8 | Polyglycidyl methacrylate | dimethylamine | 6.2 |
| 9 | Poly(1,2-butadiene) | dimethylamine | 6.2 |

EXAMPLE 10

Illustrates the Preparation of a Support

A clean glass microscope slide was partially immersed for ~10 seconds in a 0.5 percent aqueous solution of the dimthylamine adduct of expoxidized polybutadiene (Example 5B), and rinsed thoroughly under the tap with cold water. A drop of water placed on the treated surface exhibited a contact angle of 54°. The slide was completely water wettable in the unexposed areas, indicating the polymer has adsorbed on the exposed areas.

EXAMPLE 11

Illustrates the Adsorption of Protein on a Prepared Surface

Qualitatively, adsorption of protein was shown by contacting a portion of a prepared glass microscope slide (Example 10) with a 10 mg/ml solution of bovine serum albumin in pH 7 phosphate buffer for ~10 minutes. This was followed by thorough rinsing with water. Three distinct surfaces were found and could be characterized by the behavior of a water droplet in each area: in the area containing bound protein, the water drop spread; in the area containing attached polymer, the water drop beaded up; in the area of untreated glass, the water drop spread.

EXAMPLE 12

Illustrates the Adsorption of an Enzyme on a Prepared Surface

Clean pyrex glass beads (2 mm, 69.8 g) were treated with sufficient 0.1 percent aqueous solution of the dimethylamine adduct of epoxidized polybutadiene to cover the beads and allowed to stand for 15 minutes. The liquid was decanted, and the beads were washed ten times with 50 ml of deionized water and allowed to air dry.

The beads were then placed in a 50 ml burette and a solution of catalase diluted 1:25 with pH 7 phosphate buffer was added to cover the beads. After standing 5 minutes, the column was drained and rinsed with pH 7 phosphate buffer.

A substrate solution was prepared from 0.6 ml 30 percent $H_2O_2$ plus 100 ml pH 7 phosphate buffer. When the substrate solution was passed through the column at a flow rate of ~6 ml/min., no hydrogen peroxide could be detected in the eluate by the starch iodide test. Vigorous bubbling ($O_2$) was also observed in the column indicating retention of enzmatic activity.

EXAMPLE 13

Illustrates the Preparation of a Quartz Powder Adsorbent and the Adsorption of Human Serum Albumin Quartz powder (50.0 g, 1.2 $m^2$/g surface area) was combined with 500 ml of a 318 µg/ml solution of the polymer of Example 1 in water, and the slurry agitated on a flat-bed shaker for 18 hours at room temperature. The powder was recovered by filtration and washed five times by resuspending in 500 ml distilled water. The final rinse solution was found to be neutral to phenol red indicator (0.005%). The powder was dried in vacuo at room temperature.

Attachment of Serum Albumin

Three ml aliquots of human serum albumin solutions (see below) in 0.02 M pH 7.0 phosphate buffer were combined with 2.0 g of the above treated quartz powder and the slurry gently agitated overnight at room temperature. The slurry was filtered using a 0.2µ Millipore ® filter membrne to remove solids and the filtrate analyzed for protein using the Biuret method[1]. In this manner the amount of protein adsorbed per gram of powder (or per unit surface area) can be determined. The results for a range of human serum albumin concentrations are given below:

[1] S. Chaylkin, "Biolchemistry Laboratory Techniques," Wiley, N.Y., N.Y., p. 17.

| Original Albumin Conc.(mg/ml) | Equilibrium* Albumin Conc.(mg/ml) | Amount Albumin Attached mg protein/g |
|---|---|---|
| 12.0 | 10.50 | 2.25 |
| 10.5 | 9.20 | 1.95 |
| 9.0 | 7.70 | 1.95 |
| 7.5 | 6.20 | 1.95 |
| 4.5 | 3.20 | 1.95 |
| 2.4 | 1.18 | 1.83 |
| 1.2 | 0.15 | 1.20 |

*After filtration

EXAMPLE 14

Illustrates the Adsorption of a an Enzyme

A solution of 1.000 g urease[2] (3400 units/g, 7.9% nitrogen) in 50.0 ml of 0.02 M phosphate, (pH 6.9) was prepared and filtered through a bed of Celite ® (Johns-Manville Corp.) to remove undissolved solids. A 3.0 ml aliquot of the filtrate was then combined with 2.0 g of prepared quartz powder (Example 7, para. 1) and the slurry gently shaken for 6 hours at room temperature. The powder was recovered by filtration and washed thoroughly with 0.02 M phosphate followed by distilled water. Kjeldahl nitrogen analysis of the powder indicated 0.24 percent total protein or 2.4 mg urease (as total protein) per g of powder.

[2] Sigma Chemical Co., St. Louis, No.

The activity of the immobilized urease was determined using standard assay procedures[3]. The immobilized enzyme was found to have retained ~90°% of the activity of an equivalent amount of urease powder.

EXAMPLE 15

Illustrates the Adsorption of an Antigen and the Immunological Reaction Thereof

This example illustrates the attachment of immunologically active proteins (IgG) to piezoelectric quartz crystal oscillators.

Preparation of the Oscillators

10 MHz (fundamental)AT cut quartz crystal oscillators (0.3 cm diameter) mounted in MIL type HC-6/U holders were surface treated by soaking overnight in a 0.06% aqueous solution of poly(2-hydroxy-3-dimethylamino-1,4-butane) (Example 5B) with stirring at room temperature. The crystals were washed of excess polymer by flooding with a copious quantity of deionized $H_2O$ and then dried in stream of nitrogen. After equilibration at ~50% relative humidity the base frequency of the crystals was determined.

The immunologically active protein (antigen) employed was human gamma globulin (IgG, Cohn Fraction II[3]). A 10 mg/ml solution of this material in 0.02 m phosphate buffered saline (PBS, pH 7.0) was prepared and the solution allowed to stand overnight at 4° C. The clear supernatant was decanted and immediately filtered through Whatman No. 1 filter paper. The polymer treated oscillators were incubated in the IgG solution at room temperature for four hours. The solution was then flooded with PBS followed by sufficint deionized water such that no absorbable substances remained in the oscillator treatment bath. After drying in a nitrogen stream and equilibration at 50% R.H., the resultant frequency of each oscillator was determined. The composite IgG-Crystals contain a very uniform amount of protein, corresponding in this case to a frequency shift of 580±63 Hz.

These crystals react with soluble antibody to IgG and show a frequency change or weight gain directly proportional to the concentration of antibody in an assay solution. A detailed description of the assay method is disclosed in copending application Ser. No. 851,491, filed Nov. 14, 1977 assigned to the assignee of the present application.

What is claimed is:

1. An article to which biologically active proteins can be attached so as to retain substantially all of their biological activity comprising:

a solid polar support having on the surface thereof a monolayer about 10 to 250Å thick of a water soluble polymer having repeating units containing a β-hydroxyalkylene-amine moiety wherein the equivalent weight of said polymer based on said moiety is 87 to 10,000.

2. The article according to claim 1 wherein said moiety is selected from the group consisting of:

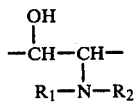   (1)

wherein $R_1$ is hydrogen or an alkyl group havng one to eight carbon atoms, $R_2$ is alkyl, having one to eight carbon atoms, or $R_1$ and $R_2$ together with the nitrogen atom to which they are attached form a heterocyclic ring; and

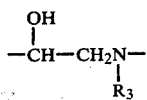   (2)

wherein $R_3$ is hydrogen or an alkyl group having one to eight carbon atoms.

3. The article according to claim 1 wherein the repeating unit of said polymer is selected from the group consisting of:

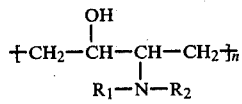   (1)

wherein $R_1$ is hydrogen or an alkyl group having one to eight carbon atoms, $R_2$ is an alkyl group having one to eight carbon atoms, or $R_1$ and $R_2$ taken together with the nitrogen atom to which they are attached form a heterocyclic ring; and

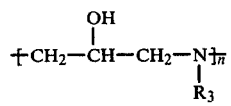   (2)

wherein $R_3$ is hydrogen or an alkyl group having one to eight carbon atoms; and

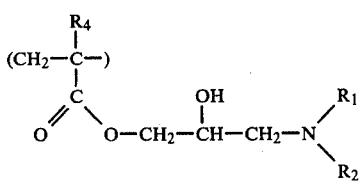   (3)

wherein $R_1$ is hydrogen or an alkyl group having one to eight carbon atoms $R_2$ is an alkyl group having one to eight carbon atoms or $R_1$ and $R_2$ taken together with the nitrogen atom to which they are attached form a heterocyclic ring, and $R_4$ is hydrogen or methyl.

4. The article according to claim 1 wherein the repeating unit of said polymer is selected from the group consisting of: (1) the dimethylamine adduct of epoxidized poly-cis-1,4-butadiene; (2) the dimethylamine adduct of epoxidized styrene-b-butadiene; (3) the dimethylamine adduct of polyglycidyl methacrylate; (4) the piperidine adduct of epoxidized styrene-b-butadiene; (5) the piperidine adduct of poly-cis-1,4-butadiene; and (6) the condensation product of epichlorohydrin and methylamine.

5. The article according to claim 4 wherein the repeating unit of said polymer is the dimethylamine adduct of epoxidized poly-cis-1,4-butadiene.

6. The article according to claim 1 wherein said support is selected from the group consisting of barium ferrite, ceramics, siliceous materials, hydroxy apatite, silver and nickel.

7. The article according to claim 1 wherein said support is a piezoelectric oscillator.

8. The article according to claim 7 wherein said oscillator is a quartz crystal.

9. The article according to claim 1 further comprising a biologically active protein attached to the surface of said article.

10. The article according to claim 9 wherein said biologically active protein is an enzyme.

11. The article according to claim 10 wherein said enzyme is selected from the group consisting of urease, glucose oxidase, invertase, catalase, papain, lipase, cellulose, dextranse, amylase, ribonuclease, carboxypeptidase and urokinase.

12. The article according to claim 9 wherein said biologically active protein is an immunologically active protein.

13. The article according to claim 12 wherein said immunologically active protein is selected from the group consisting of: gamma globulins; haptoglobin; $β_1$-antitryspin inhibitor; serum albumin and transferrin.

14. The article according to claim 11 wherein said support is a piezoelectric oscillator.

15. The article according to claim 14 wherein said oscillator is a quartz crystal.

16. The article according to claim 15 wherein the repeating unit of said polymer is the dimethylamine adduct of epoxidized poly-cis-1,4-butadiene.

17. A method of immobilizing a biologically active protein on a solid polar support comprising the steps of: (1) applying to said support a monolayer about 10 to 250Å thick of a water-soluble polymer having repeating units containing a β-hydroxyalkyleneamine moiety wherein the equivalent weight of said polymer based on said moiety is 87 to about 10,000, wherein said monolayer is applied to said support by immersing said support in an aqueous solution of said water-soluble polymer followed by thorough rinsing of said support with water; and (2) contacting the treated support formed in step (1) with an aqueous solution of biologically active protein.

18. The method according to claim 17 wherein said moiety is selected from the group consisting of:

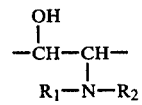   (1)

wherein $R_1$ is hydrogen or an alkyl group having one to eight carbon atoms, $R_2$ is an alkyl group having one to eight carbon atoms, or $R_1$ and $R_2$ together with the nitrogen atom to which they are attached form a heterocyclic ring; and

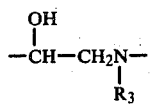

(2)

wherein $R_3$ is a hydrogen or an alkyl group having one to eight carbon atoms.

19. The method according to claim 17 wherein the repeating unit of said polymer is selected from the group consisting of:

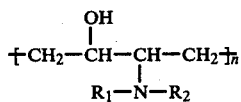

(1)

wherein $R_1$ is hydrogen or an alkyl group having one to eight carbon atoms, $R_2$ is an alkyl group having one to eight carbon atoms, or $R_1$ and $R_2$ taken together with the nitrogen atom to which they are attached form a heterocyclic ring;

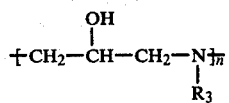

(2)

wherein $R_3$ is hydrogen or an alkyl group having one to eight carbon atoms; and

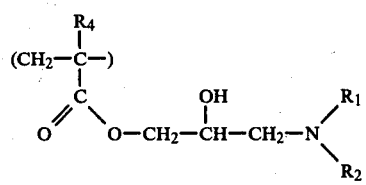

(3)

wherein $R_1$ is hydrogen or an alkyl group having one to eight carbon atoms, $R_2$ is an alkyl group having one to eight carbon atoms or $R_1$ and $R_2$ taken together with the nitrogen atom to which they are attached form a heterocyclic ring, and $R_4$ is hydrogen or methyl.

20. The method according to claim 19 wherein the repeating unit of said polymer is: (1) the dimethylamine adduct of epoxidized poly-cis-1,4-butadiene; (2) the dimethyalmine adduct of epoxidized styrene-b-butadiene; (3) the dimethylamine adduct of polyglycidyl methacrylate; (4) the piperidine adduct of epoxidized styrene-b-butadiene; (5) the piperidine adduct of poly-cis-1,4-butadiene; and (6) the condensation product of epichlorohydrin and methylamine.

21. The method according to claim 19 wherein the repeating unit of said polymer is the dimethylamine adduct of epoxidized poly-cis-1,4-butadiene.

22. The method according to claim 19 wherein said support is selected from the group consisting of barium ferrite, caramics, siliceous materials, hydroxy apatite, silver and nickel.

23. The method according to claim 22 wherein said support is a piezoelectric oscillator.

24. The method according to claim 23 wherein said oscillator is a quartz crystal.

25. The method according to claim 19 wherein said biologically active protein is an enzyme.

26. The method according to claim 25 wherein said enzyme is selected from the group consisting of urease, glucose oxidase, invertase, catalase, papain, lipase, celluloase, dextranase, amylase, ribonuclease, carboxypeptidase and urokinase.

27. The method according to claim 19 wherein said biologically active protein is an immunologically active protein.

28. The method according to claim 27 wherein said immunologically active protein is selected from the group consisting of gamma globulins, haptoglobin, $\gamma_1$-antitrypsin inhibitor, serum albumin and transferrin.

29. The method according to claim 27 wherein said support is a piezoelectric quartz crystal oscillator.

30. The method according to claim 29 wherein the repeating unit of said polymer is the dimethylamine adduct of poly-cis-1,4-butadiene.

* * * * *